US009846128B2

(12) United States Patent
Ilan et al.

(10) Patent No.: US 9,846,128 B2
(45) Date of Patent: Dec. 19, 2017

(54) INSPECTION SYSTEM AND A METHOD FOR EVALUATING AN EXIT PUPIL OF AN INSPECTION SYSTEM

(71) Applicant: Applied Materials Israel, Ltd., Rehovot (IL)

(72) Inventors: Harel Ilan, Rehovot (IL); Ido Kofler, Givataim (IL); Ido Dolev, Rehovot (IL)

(73) Assignee: APPLIED MATERIALS ISRAEL LTD., Rehovot (IL)

( * ) Notice: Subject to any disclaimer, the term of this patent is extended or adjusted under 35 U.S.C. 154(b) by 0 days.

(21) Appl. No.: 15/001,099

(22) Filed: Jan. 19, 2016

(65) Prior Publication Data

US 2017/0205359 A1    Jul. 20, 2017

(51) Int. Cl.
*G01N 21/95* (2006.01)

(52) U.S. Cl.
CPC .................. *G01N 21/9505* (2013.01)

(58) Field of Classification Search
CPC ........... G01N 21/9505; G01N 21/9501; G01N 21/8806; G01N 21/6489; G01N 21/94; G01N 21/1717; G01N 21/8422; G01N 21/47; G01N 2021/95676; G01N 21/95692; G01N 2021/8864; G01N 2201/103; G01N 2201/0668; H01L 2924/0002; H01L 22/12; G03F 1/84; G02F 1/133514; G02F 1/1334; G02F 1/133512; G02F 1/1393; G02F 1/13394; G02F 1/133753; G02F 1/136227

See application file for complete search history.

(56) References Cited

U.S. PATENT DOCUMENTS

| 6,813,058 | B1 * | 11/2004 | Sandstrom | G03B 27/44 359/290 |
|---|---|---|---|---|
| 7,940,384 | B2 * | 5/2011 | Hill | G01N 21/9501 356/237.3 |
| 9,377,290 | B2 * | 6/2016 | Yun | A61B 5/0059 |
| 9,518,916 | B1 * | 12/2016 | Pandev | G01N 21/255 |
| 9,632,039 | B2 * | 4/2017 | Den Boef | G01N 21/956 |
| 2005/0078293 | A1 * | 4/2005 | Mackey | G03F 7/70091 355/69 |
| 2007/0279630 | A1 * | 12/2007 | Kandel | G03F 7/70633 356/401 |
| 2009/0028423 | A1 * | 1/2009 | Sandstrom | G01N 21/956 382/149 |

(Continued)

*Primary Examiner* — Tarifur Chowdhury
*Assistant Examiner* — Mohamed K Amara
(74) *Attorney, Agent, or Firm* — Kilpatrick Townsend & Stockton LLP

(57) ABSTRACT

An inspection system that may include a first detection module, an illumination and collection module, and a processor. The illumination and collection module and the first detection module may be configured to execute one or more illumination and collection iterations. Each inspection iteration may include: illuminating with illuminating radiation multiple points of an object; (ii) directing first collected radiation from the multiple points of the object through one or more first exit pupil regions towards the first detection module; and (iii) generating first detection signals that may be indicative of the first collected radiation. The processor may be configured to process the first detection signals to provide a first mapping between (i) a characteristic of radiation at the first exit pupil, (ii) the multiple points of the object, and (iii) the multiple first exit pupil regions.

15 Claims, 12 Drawing Sheets

(56) References Cited

U.S. PATENT DOCUMENTS

| | | | |
|---|---|---|---|
| 2010/0046092 A1* | 2/2010 | Shmarev | G01N 21/47 359/728 |
| 2012/0019816 A1* | 1/2012 | Shibata | G01N 21/21 356/237.5 |
| 2012/0092636 A1* | 4/2012 | Van Der Mast | G03F 7/70616 355/67 |
| 2012/0296576 A1* | 11/2012 | Shibata | G01B 11/303 702/40 |
| 2012/0327503 A1* | 12/2012 | Manassen | G01J 1/4257 359/291 |
| 2013/0188160 A1* | 7/2013 | Ruoff | G03F 7/70116 355/52 |
| 2014/0146297 A1* | 5/2014 | Vainer | G01N 21/94 355/30 |
| 2015/0145151 A1* | 5/2015 | Van Der Schaar | G03F 7/70633 257/797 |
| 2016/0011523 A1* | 1/2016 | Singh | G01J 3/2823 355/77 |
| 2016/0118265 A1* | 4/2016 | Goddard | H01L 21/30604 438/71 |
| 2016/0341945 A1* | 11/2016 | Ou | H04N 7/18 |
| 2017/0025247 A1* | 1/2017 | Stevens | H01J 37/222 |
| 2017/0061604 A1* | 3/2017 | Pandev | G06T 7/0004 |

* cited by examiner

INSPECTION SYSTEM AND A METHOD FOR EVALUATING AN EXIT PUPIL OF AN INSPECTION SYSTEM

BACKGROUND

A variety of systems are used for automated inspection of objects such as semiconductor wafers, in order to detect defects, particles and/or patterns on the wafer surface as part of a quality assurance process in semiconductor manufacturing processes. It is a goal of current inspection systems to have high resolution and high contrast imaging in order to provide the reliability and accuracy demanded in sub-micron semiconductor manufacturing processes.

Various inspection systems have a masking module that controls the collection of beams that are scattered or reflected from the object. A masking module includes a predefined and limited number of apertures and the inspection system may select which of the apertures to use.

There is a growing need to evaluate existing masking modules and to evaluate future masking modules.

SUMMARY

According to an embodiment of the invention there may be provided a system that may include a first detection module; an illumination and collection module; a processor; wherein the illumination and collection module and the first detection module may be configured to execute one or more illumination and collection iterations; wherein each inspection iteration may include: (i) illuminating, by the illumination and collection module and with illuminating radiation, multiple points of an object; (ii) directing, by the illumination and collection module, first collected radiation from the multiple points of the object through one or more first exit pupil regions towards the first detection module; wherein one or more first exit pupil regions belong to multiple first exit pupil regions; wherein the multiple first exit pupil region belong to a first exit pupil; and (iii) generating, by the first detection module, first detection signals that may be indicative of the first collected radiation. The processor may be configured to process the first detection signals to provide a first mapping between (i) a characteristic of radiation at the first exit pupil, (ii) the multiple points of the object, and (iii) the multiple first exit pupil regions.

The illumination and collection module and the first detection module may be configured to execute multiple illumination and collection iterations; wherein during each inspection iteration the first collected radiation passes only through a single first exit pupil region.

The different illumination and collection iterations of the multiple illumination and collection iterations may be associated with different first exit pupil regions of the multiple first exit pupil regions.

The first detection module may include multiple first detectors that may be spaced apart from the first exit pupil, and wherein the illumination and collection module may include a first masking module that may be configured to selectively unmask the single first exit pupil region per illumination and collection iteration.

The multiple illumination and collection iterations may include a plurality of inspection iteration sets; wherein each inspection iteration set may include: (a) a first inspection iteration during which a single beam of illumination radiation scans the multiple points of the object and the collected radiation passes through a predefined first exit pupil region; (b) a second inspection iteration during which a pair of beams of illumination radiation that impinge on the object to provide a pair of spots that (i) may be spaced apart from each other by a predefined difference and (ii) scan the multiple points of the object; and wherein the collected radiation passes through the predefined first exit pupil region; and (c) a third inspection iteration during which another pair of beams of illumination radiation that impinge on the object to provide another pair of spots that (i) may be phase shifted from each other by a predefined phase shift and (ii) scan the multiple points of the object; and wherein the collected radiation passes through the predefined first exit pupil region.

The processor may be configured to calculate an S-matrix in response to the first detection signals.

The first detection module may include multiple first detectors that may be spaced apart from the first exit pupil, wherein the illumination and collection module may include a first masking module that may be configured to selectively mask different first exit pupil regions of the multiple first exit pupils.

The illumination and collection module may be configured to execute a single inspection iteration during which the first collected radiation passes through the multiple first exit pupil regions.

The first detection module may include multiple first detectors that may be positioned at the first exit pupil, and wherein at least one first detector of the multiple first detectors may be allocated per each first exit pupil region.

The illumination and collection module may be configured to direct the first collected radiation through the multiple first exit pupil regions.

The processor may be configured to evaluate, in response to the first mapping, an outcome of a first masking operation that masks at least one masked first exit pupil region while unmasking at least one unmasked first exit pupil region; and wherein the at least one masked first exit pupil region and the at least one at least one unmasked first exit pupil region belong to the multiple first exit pupil regions.

The characteristic of radiation at the first exit pupil may be an intensity of the radiation at the first exit pupil, and wherein the processor may be configured to evaluate the first masking operation by summing, for each of the multiple points of the objects, detections signals associated only with the at least one unmasked first exit pupil region.

The system may include a second detection module; wherein each inspection iteration further may include directing second collected radiation from the multiple points of the object through one or more second exit pupil regions towards the second detection module and generating second detection signals indicative of the second collected radiation; wherein the one or more second exit pupil regions belong to multiple second exit pupil regions of a second exit pupil.

The system may be configured to pass the second collected radiation through a same one or more second exit pupil regions during different illumination and collection iterations.

The processor may be configured to compare second detection signals obtained during the different illumination and collection iterations to provide comparison results; and to align first detection signals obtained during the different illumination and collection iterations based on the comparison results.

The processor may be configured to process the second detection signals to provide a second mapping between (i) a characteristic of radiation at the second exit pupil, (ii) the multiple points of the object, and (iii) the multiple second exit pupil regions.

The second collected radiation may be scattered from the multiple points of the object and wherein the first collected radiation may be reflected from the multiple points of the object.

The characteristic of radiation at the first exit pupil may be an intensity of the radiation at the first exit pupil.

The multiple points of the object may form a continuous area of the object.

According to an embodiment of the invention there may be provided a method that may include executing one or more illumination and collection iterations; wherein each inspection iteration may include: (i) illuminating, with illuminating radiation, multiple points of the object, (ii) directing first collected radiation from the multiple points of the object through one or more first exit pupil regions towards a first detection module; wherein one or more first exit pupil regions belong to multiple first exit pupil regions of a first exit pupil; and (iii) generating, by the first detection module, first detection signals indicative of the first collected radiation; and processing, by a processor, the first detection signals to provide a first mapping between (i) a characteristic of radiation at the first exit pupil, (ii) the multiple points of the object, and (iii) the multiple first exit pupil regions.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
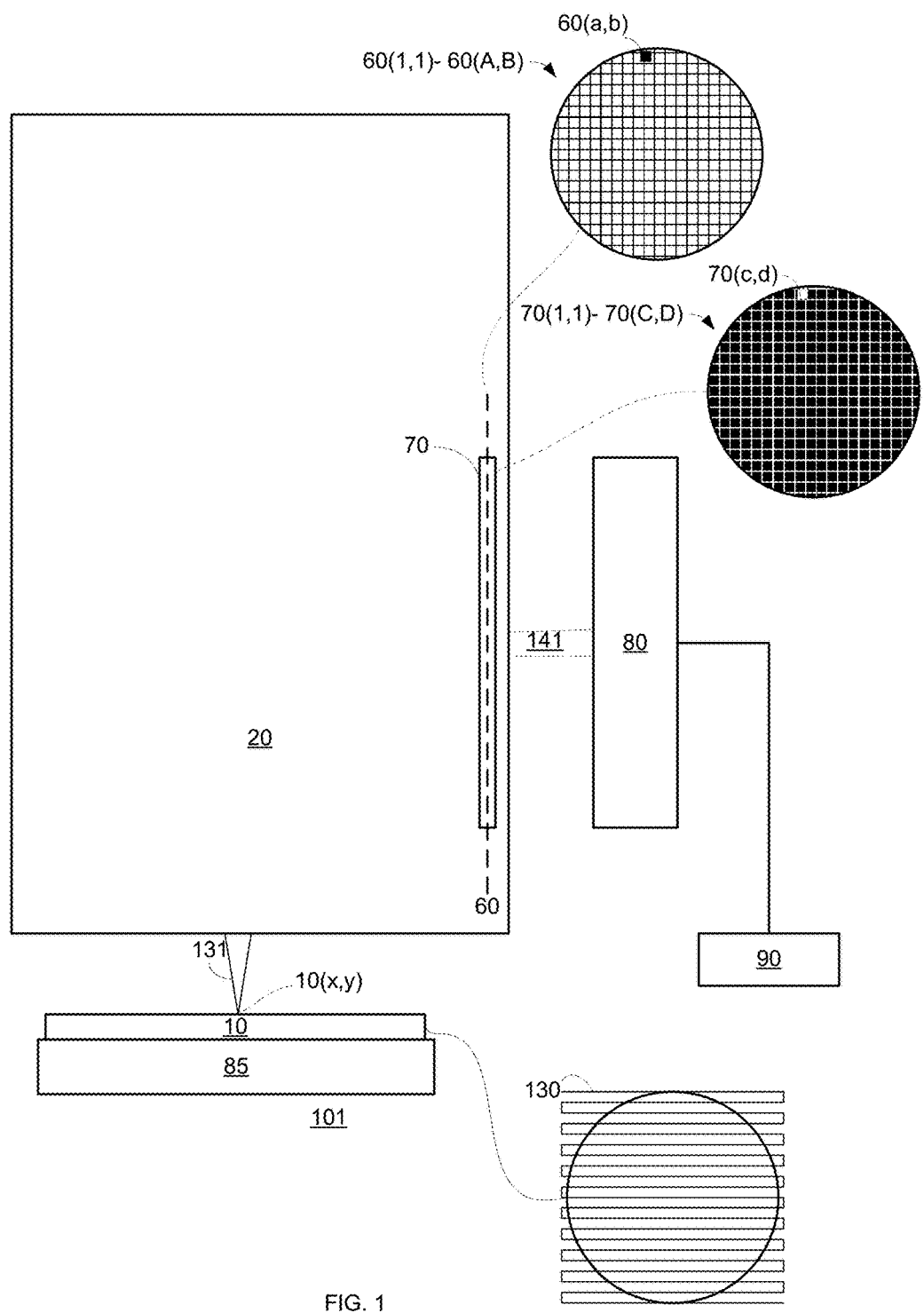
FIG. 1 illustrates a system and an object according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that may be executed by the system and should be applied mutatis mutandis to a non-transitory computer readable medium that stores instructions that may be executed by the system.

Any reference in the specification to a non-transitory computer readable medium should be applied mutatis mutandis to a system capable of executing the instructions stored in the non-transitory computer readable medium and should be applied mutatis mutandis to method that may be executed by a computer that reads the instructions stored in the non-transitory computer readable medium.

The following detailed description is of exemplary embodiments of the invention but the invention is not limited thereto, as modifications and supplemental structures may be added, as would be apparent to those skilled in the art. In particular, but without limitation, while an exemplary embodiment may be disclosed with regard to the inspection of a subject surface by detecting reflected light using a light source and detecting unit that are disposed on a common side of an object (a "reflective system"), it would be readily apparent to one skilled in the art that the teachings are readily adaptable to the inspection of an object by detecting transmitted light with a detecting unit that is on a side of an object opposite to that of the light source (a "transmissive system").

While the reflective system and the transmissive system differ, for one example by the absence of a beam splitter in the transmissive system, the principles of the present invention are applicable to both types of systems. As would be understood by one skilled in the art, both types of systems may be utilized separately or together in the inspection of an object, in accordance with the present invention.

FIG. 1 illustrates system 101 and object 10 according to an embodiment of the invention.

Without limitation and only by example, object 10 may be any semiconductor product having multiple semiconductor devices thereon, at any of several stages of manufacture, or may be a mask, reticule or the like used in a manufacturing process, where such object must be inspected for defects, foreign objects or pattern accuracy.

System 101 is illustrated as including illumination and collection module 20, first detection module 80, processor 90 and mechanical stage 85.

Mechanical stage 85 is configured to support object 10 and introduce a mechanical movement between object 10 and the illumination and collection module 20.

In FIG. 1 the mechanical movement follows a raster scan pattern 130 that scans the entire object 10. It is noted that scan patterns other than a raster scan pattern can be applied. It is further noted that the scan pattern may scan only one or more parts of object 10.

According to an embodiment of the invention, instead of moving the object 10 (as shown in FIG. 1) the illumination and collection module 20 can be mechanically moved. Alternatively—both object 10 and illumination and collection module 20 can be mechanically moved during the scan of object 10.

Illumination and collection module 20 and first detection module 80 are configured to execute one or more illumination and collection iterations.

During each inspection iteration illumination and collection module 20 is configured to (i) illuminate, by illuminating radiation (such as illuminating beam 131), multiple points of the object; and (ii) direct first collected radiation (such as collected beam 141) from the multiple points of the object through one or more first exit pupil regions towards the first detection module.

The multiple points of the object may be scanned by a single illuminating beam in a serial manner. Alternatively, the multiple points of the object may be scanned with a plurality of illuminating beams.

The multiple points of object 10 may cover the entire object or only one or more parts of object 10. It is assumed, for simplicity of explanation that the multiple points of the object form cover the entire object.

Illumination and collection module 20 may include first masking module 70 that is positioned at first exit pupil 60.

First exit pupil 60 include multiple first exit pupil regions 60(1,1)-60(A,B). In FIG. 1 first exit pupil region 60($a,b$) is represented by a black box. The first exit pupil regions may be of the same size and shape. Alternatively—at least two of the first exit pupil regions may differ from each other by size or shape.

First masking module 70 may selectively mask includes first masking elements 70(1,1)-70(C,D) for selectively masking any first exit pupil region out of multiple first exit pupil regions 60(1,1)-60(A,B). There may be one or more first masking elements per first exit pupil region. In FIG. 1 first masking element 70($c,d$) is represented by a black box. First masking element 70($c,d$) unmasks the first exit pupil region 60($a,b$).

In FIG. 1 first masking module 70 is illustrated as unmasking only a single first exit pupil region 60($a,b$).

According to an embodiment of the invention there are multiple (R) first exit pupil regions and the first masking module 70 is configured to unmask only one first exit pupil region per illumination and collection iteration.

Executing R illumination and collection iterations, each illumination and collection iterations involving unmasking a different first exit pupil region, may provide information about each one of the first exit pupil regions 60(1,1)-60(A, B).

It is noted that the masking module 70 may be configured to unmask any combination of first exit pupil regions at any illumination and collection iteration.

During each inspection iteration the first detection module 80 is configured to generate first detection signals indicative of the first collected radiation.

In FIG. 1 first detection module 80 is spaced apart from first exit pupil 60.

Processor 90 is configured to process first detection signals obtained during the one or more illumination and collection iterations and to provide a first mapping between (i) a characteristic of radiation at the first exit pupil, (ii) the multiple points of the object, and (iii) the multiple first exit pupil regions.

It is assumed, for simplicity of explanation, that the characteristic of the radiation is the intensity of the radiation.

Each inspection iteration may provide a two dimensional scan image Uab(x,y)—wherein "ab" represents the first exit pupil region (60($a,b$)) that was unmasked during the illumination and collection iteration.

When performing multiple (R) illumination and collection iterations during which information about each first exit pupil was obtained, the first mapping may provide the intensity of the radiation for each combination of first exit pupil region 60($a,b$) and for each point 10($x,y$) of the multiple points of the object. The first mapping may be represented by a four dimensional function U(a,b,x,y).

By adding, per point of the object, the values obtained during each of the multiple (R) illumination and collection iterations, a pupil image may be obtained. Uxy(a,b) is calculated by a slicing the four dimensional function to a two dimensional function by fixing the x and y coordinates.

Processor 90 may use differences in the pupil image between defect locations and reference locations in order to determine which spatial filter (involving selectively masking one or more first exit pupil region) is optimal for improving the detection capability.

Processor 90 may be configured to evaluate an outcome of a first masking operation that masks at least one masked first exit pupil region while unmasking at least one unmasked first exit pupil region. The evaluating may include summing, for each of the multiple points of the objects, detections signals associated only with the at least one unmasked first exit pupil region.

For example, when evaluating a masking operation that will unmask only a set of first exit pupil regions then the processor may calculate a sample image using the selected mask associated with the set by applying the following function: Uset=Sum (for all values of a and b associated with the set of first exit pupil regions) over U(a,b,x,y).

Figure 2A:
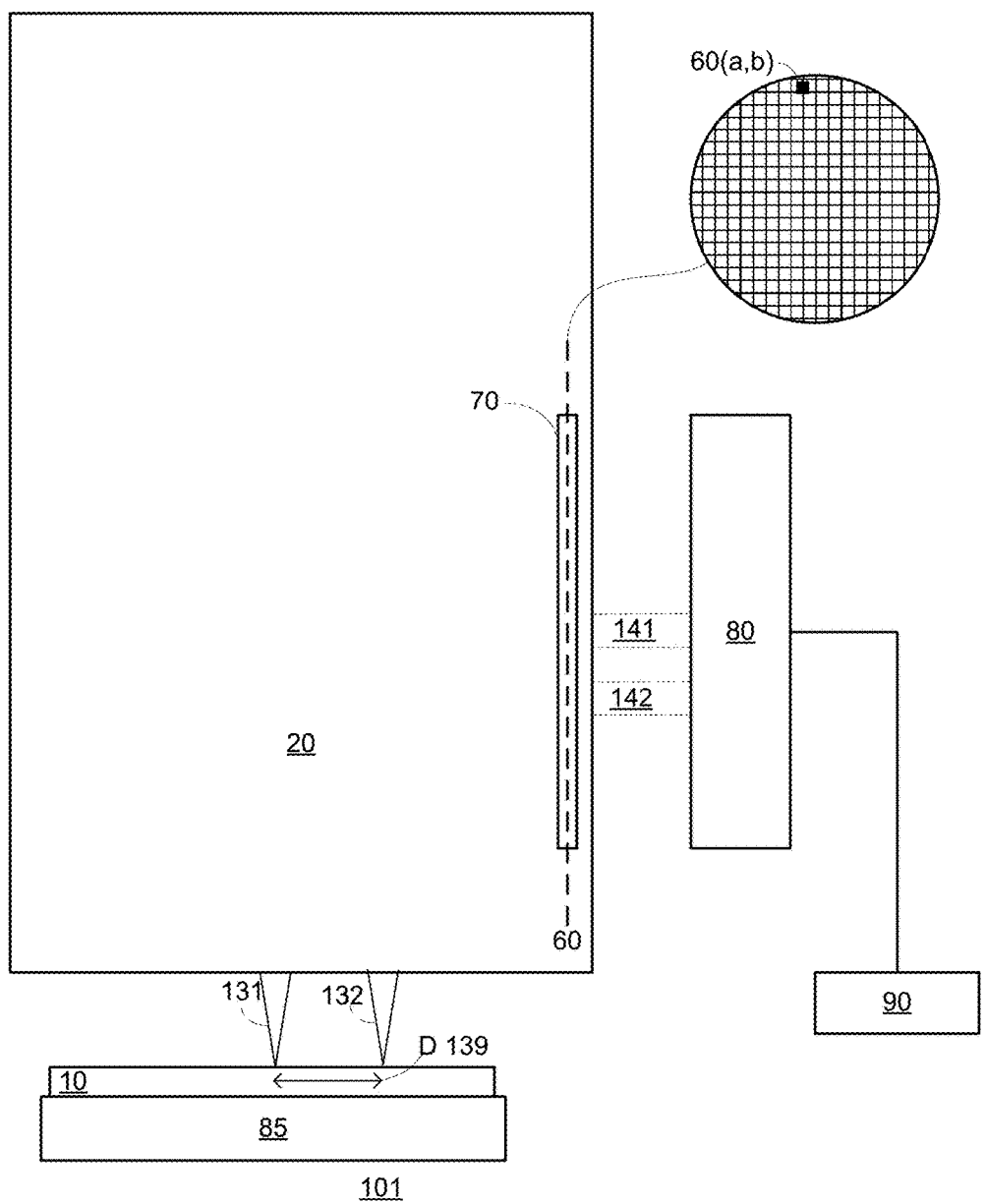
FIG. 2A illustrates a system and an object according to an embodiment of the invention.

FIG. 2A illustrates system 101 and object 10 according to an embodiment of the invention.

FIG. 2A illustrates system 101 that scans object 10 with two illuminating beams 131 and 132. Once the two illuminating beams 131 and 132 impinge on object 10 spots are formed on the object 10 that differ from each other by a predefined distance 139.

It is noted that predefined distance 139 may be large enough to prevent an interference of illuminating beams 131 and 132. Alternatively—predefined distance 139 may be a predefined distance that is small enough to allow illuminating beams 131 and 132 to interfere with each other.

In FIG. 2A first detection module 80 receives two collected beams 141 and 142.

Figure 2B:
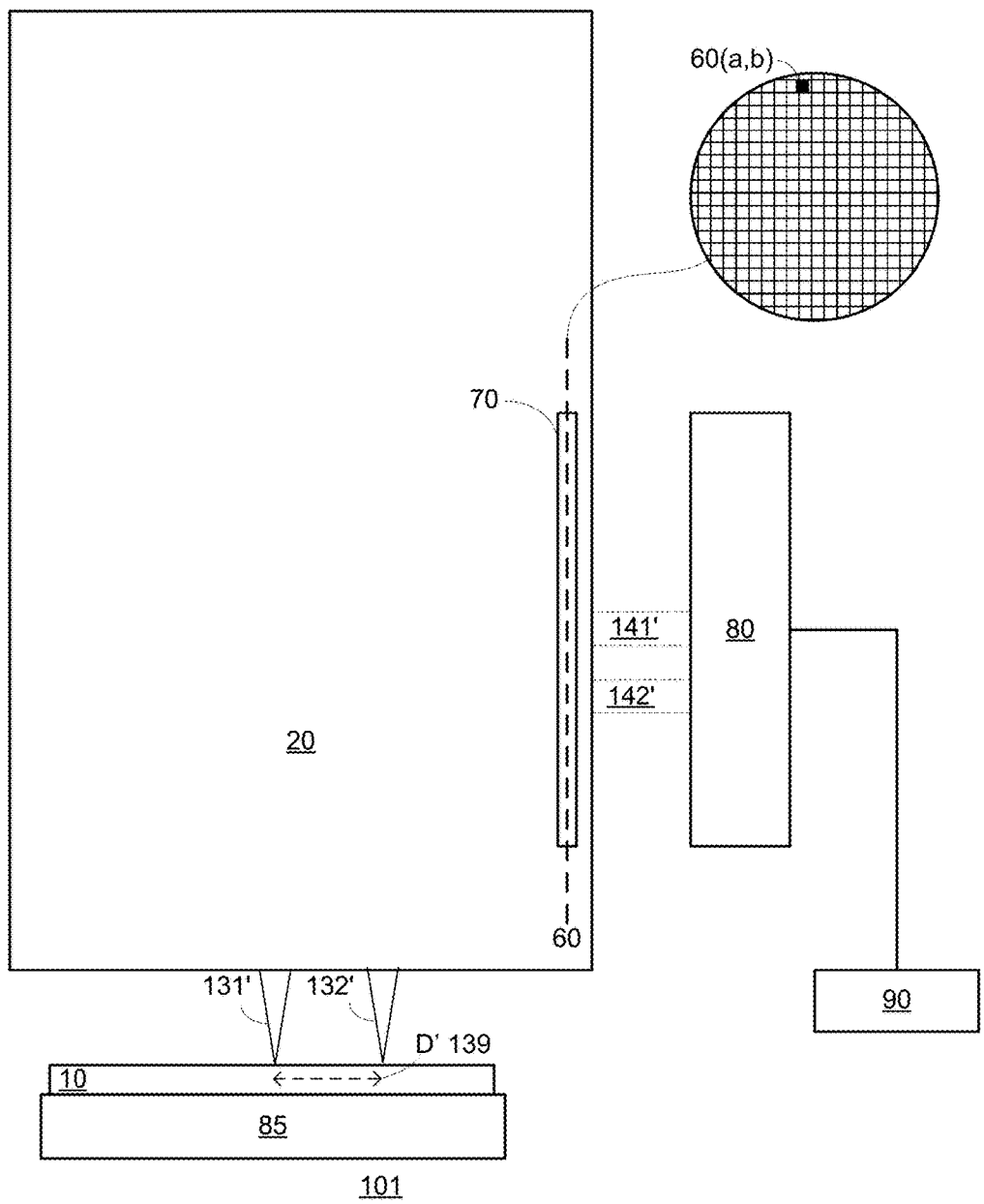
FIG. 2B illustrates a system and an object according to an embodiment of the invention.

FIG. 2B illustrates system 101 and object 10 according to an embodiment of the invention.

FIG. 2B illustrates system 101 that scans object 10 with two illuminating beams 131' and 132'. Once the two illuminating beams 131' and 132' impinge on object 10 the illuminating beams 131' and 132' are phase shifted by a predefined phase shift 139'. A non-limiting example of a predefined phase shift 139' is pi/2.

In FIG. 2B the first detection module 80 receives two collected beams 141' and 142'.

It should be noted that system 101 may scan object 10 with more than two illuminating beams.

According to an embodiment of the invention, system 101 may be configured to perform multiple (for example—3*R) illumination and collection iterations.

The multiple illumination and collection iterations include R sets of illumination and collection iterations. Different sets of illumination and collection iterations are associated with different first exit pupil regions. The R sets illumination and collection iterations "cover" the R first exit pupil regions.

Each inspection iteration set is associated with a first exit pupil region 60($a,b$) and includes a first illumination and collection iteration, a second inspection iteration and a third illumination and collection iteration.

The first inspection iteration includes scanning with a single illuminating beam (such as illuminating beam 131 of FIG. 1) the multiple points of the object and the collected radiation passes through first exit pupil region 60($a,b$).

The second inspection iteration includes scanning the multiple points of the object by a pair of beams of illumination radiation (such as illuminating beams 131 and 132 of FIG. 2A) that impinge on the object to provide a pair of spots that are spaced apart from each other by a predefined difference (denoted 139 in FIG. 2A). The collected radiation (such as collected beams 141 and 142 of FIG. 2A) passes through first exit pupil region 60($a,b$).

The third inspection iteration includes scanning the multiple points of the object by a pair of beams of illumination radiation (such as illuminating beams 131' and 132' of FIG. 2B) that impinge on the object to provide a pair of spots that are phase shifted from each other by a predefined phase shift (denoted 139' in FIG. 2B). The collected radiation (such as collected beams 141' and 142' of FIG. 2B) passes through first exit pupil region 60($a,b$).

The detection signals obtained during the first inspection iteration may be processed to provide exit pupil image denoted I(x,y).

The detection signals obtained during the second inspection iteration may be processed to provide exit pupil image denoted $I_1$(x,y).

The detection signals obtained during the third inspection iteration may be processed to provide exit pupil image denoted $I_2$(x,y).

Processor 90 may process I(x,y), $I_1$(x,y) and $I_2$(x,y).

If the complex field distribution for a single spot u(x,y) it is argued that:

$$I(x,y)=|u(x,y)|^2$$

$$I_1(x,y)=|u(x,y)+u(x+d,y)|^2=I(x,y)+I(x+d,y)+2\sqrt{I(x,y)I(x+d,y)}\cos(\Delta\varphi)$$

$$I_2(x,y)=|u(x,y)+iu(x+d,y)|^2=I(x,y)-I(x+d,y)+2\sqrt{I(x,y)I(x+d,y)}\sin(\Delta\varphi)$$

Therefore:

$$\cos(\Delta\varphi)=\frac{I_1(x,y)-I(x,y)-I(x+d,y)}{2\sqrt{I(x,y)I(x+d,y)}}$$

$$\sin(\Delta\varphi)=\frac{I_1(x,y)-I(x,y)+I(x+d,y)}{2\sqrt{I(x,y)I(x+d,y)}}$$

$$\frac{\partial\varphi}{\partial x}=\frac{1}{d}\text{atan}(\cos(\Delta\varphi),\sin(\Delta\varphi))$$

The same analysis can be done for the $$\frac{\partial\varphi}{\partial y}$$

producing the full gradient of the phase.

Finally, for each (a,b) location at the exit pupil which attributed to a wave in the s-matrix we have full phased image, therefore using the reciprocity of the s-matrix between incident and scattered waves, a full s-matrix can be reconstructed according to the spatial resolution of the pupil imaging.

Figure 3:
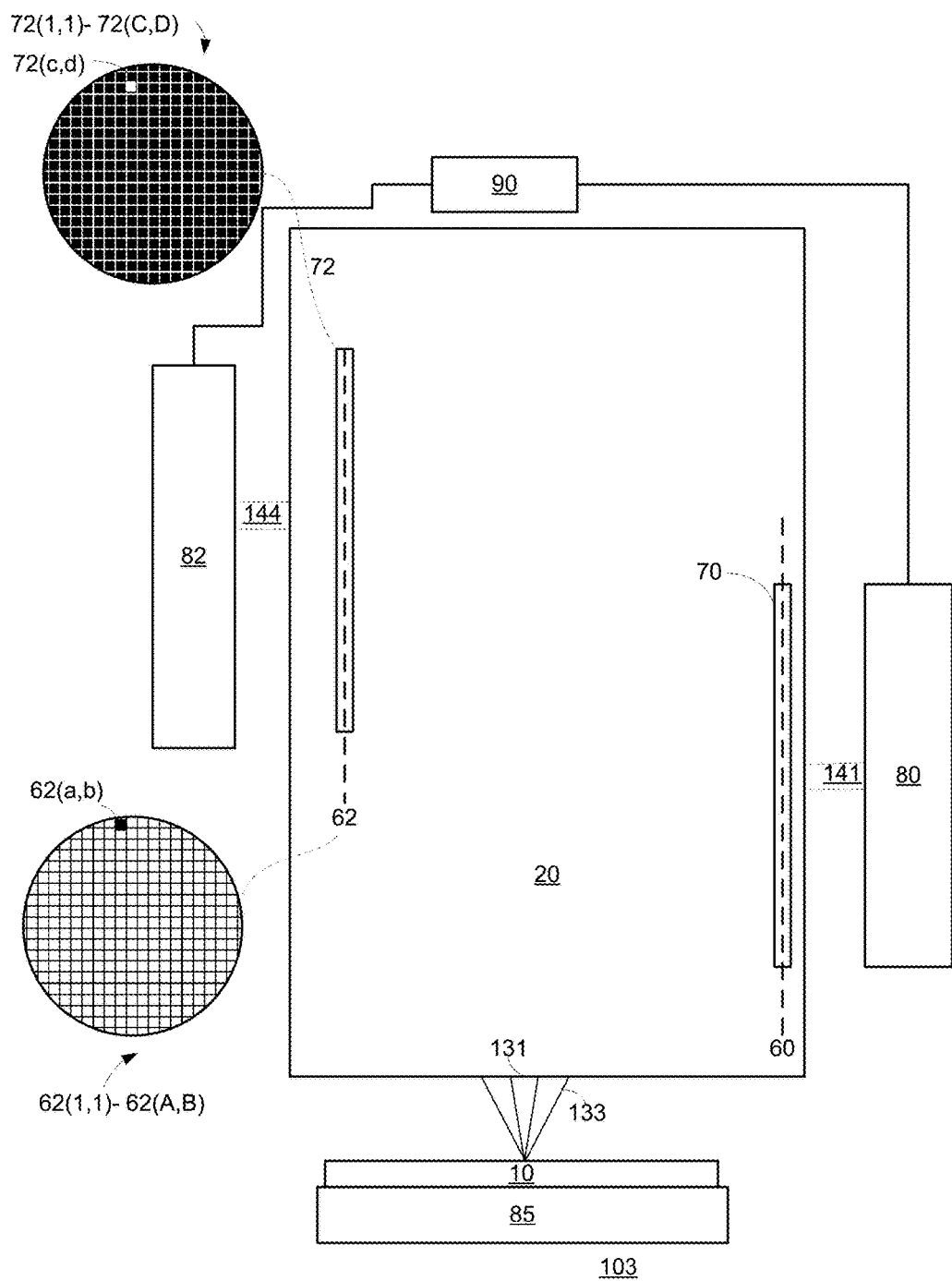
FIG. 3 illustrates a system and an object according to an embodiment of the invention.

FIG. 3 illustrates system 103 according to an embodiment of the invention.

System 103 differs from system 101 by including second exit pupil 62, second masking module 72 that is positioned at the second exit pupil 62, and second detection module 82. In FIG. 3, first detection module 80 receives first collected beam 141 and second detection module 82 receives second collected beam 142.

Second exit pupil 62 include multiple second exit pupil regions 62(1,1)-62(A,B). In FIG. 1 second exit pupil region 62($a,b$) is represented by a black box. The second exit pupil regions may be of the same size and shape. Alternatively—at least two of the second exit pupil regions may differ from each other by size or shape.

Second masking module 72 includes second masking elements 72(1,1)-72(C,D) for selectively masking any second exit pupil region out of multiple second exit pupil regions 62(1,1)-62(A,B). There may be one or more second masking elements per second exit pupil region. In FIG. 1 second masking element 72($c,d$) is represented by a black box. First masking element 72($c,d$) unmasks second exit pupil region 62($a,b$).

In FIG. 3 second masking module 72 is illustrated as unmasking only a single second exit pupil region 62($a,b$).

Multiple second exit pupil regions 62(1,1)-62(A,B) may have the same shape and size as the multiple first exit pupil regions 60(1,1)-60(A,B). Alternatively—at least one second exit pupil region may differ by shape, size or both shape and size from at least one first exit pupil region.

System 103 may be configured to execute one or more illumination and collection iterations.

During each inspection iteration illumination and collection module 20 is configured to (i) illuminate, by illuminating radiation (such as illuminating beam 131), multiple points of the object; (ii) direct first collected radiation (such as collected beam 141) from the multiple points of the object through one or more first exit pupil regions towards first detection module 80; and (iii) direct second collected radiation (such as collected beam 144) from the multiple points of the object through one or more second exit pupil regions towards second detection module 82.

During each inspection iteration, first detection module 80 is configured to generate first detection signals indicative of the first collected radiation and second detection module 82 is configured to generate second detection signals indicative of the second collected radiation.

Processor 90 may be configured to process second detection signals obtained during the one or more illumination and collection iterations and to provide a second mapping between (i) a characteristic of radiation at the second exit pupil, (ii) the multiple points of the object, and (iii) the multiple second exit pupil regions.

According to an embodiment of the invention the second masking module 72 second detection module 82 may be used for aligning first scan images obtained by first detection module 80.

In order to perform the alignment the configuration of the second masking module 72 is fixed during multiple illumination and collection iterations. The second detection module 82 obtains, during different illumination and collection iterations, different second scan images.

Processor 90 is configured to calculate misalignments between the second scan images to provide second misalignment results.

Processor 90 may also be configured to align the first scan images using the second misalignment results. The alignment of the first scan image may be based upon an assumption that a first scan image and a second scan image that were obtained during the same inspection iteration will suffer from the same misalignment.

According to an embodiment of the invention, first masking module 70 and first detection module 80 may be used for aligning second scan images obtained by second detection module 82. The alignment may be executed by (i) using, during multiple illumination and collection iterations, a first masking module 70 of a fixed configuration, (ii) calculating misalignments between the first scan images to provide first misalignment results, and (iii) aligning the second scan images using the first misalignment results.

Figure 4:
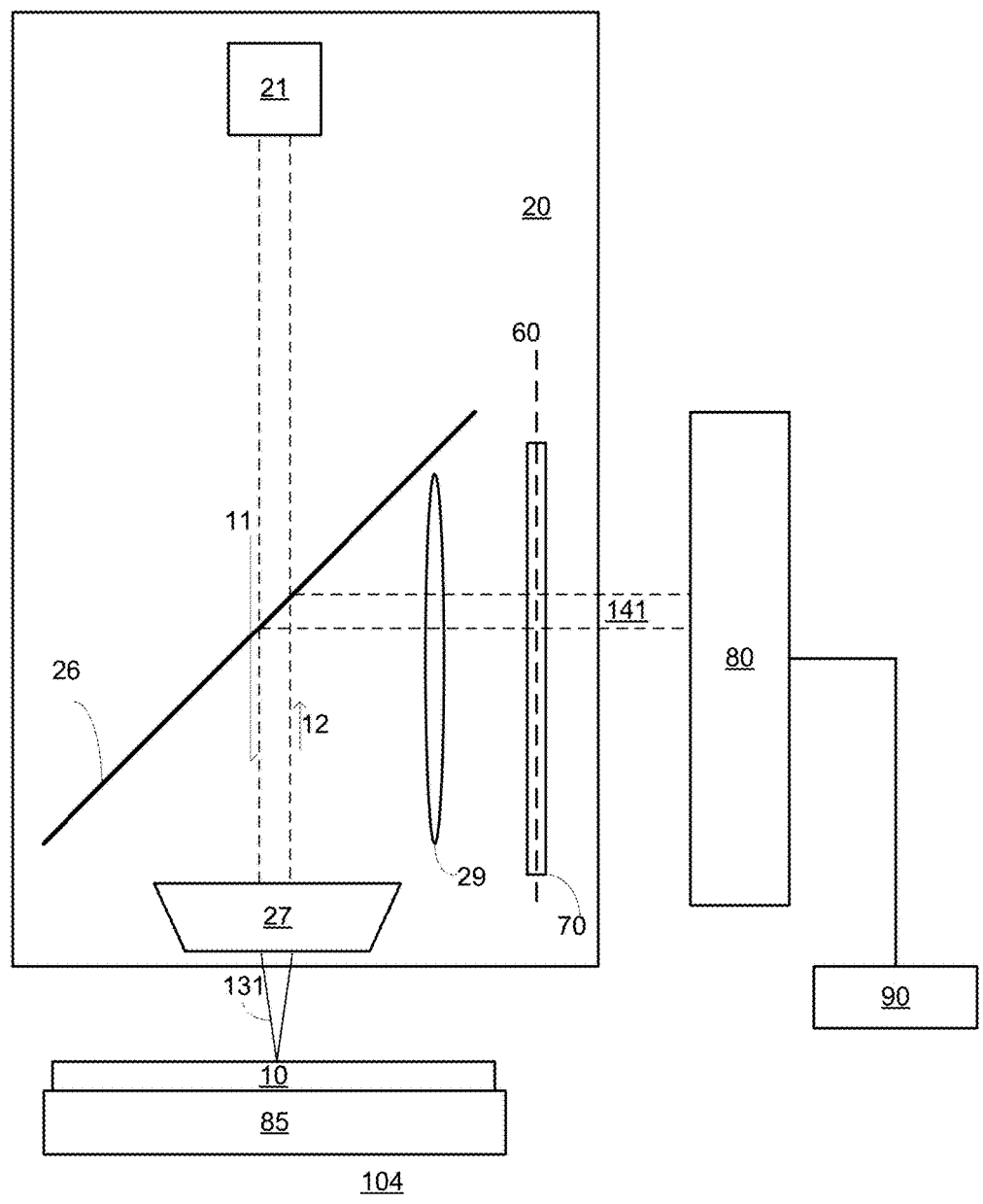
FIG. 4 illustrates a system and an object according to an embodiment of the invention.

FIG. 4 illustrates system 104 and object 10 according to an embodiment of the invention.

System 104 is illustrated as including illumination and collection module 20, first detection module 80, processor 90 and mechanical stage 85.

Illumination and collection module 20 is illustrated as including a radiation source 21, first beam splitter 26, objective lens 27, lens 29, and first masking module 70 that is positioned at first exit pupil 60.

Radiation source 21 directs first radiation beam 11 towards first beam splitter 26.

First radiation beam 11 passes through first beam splitter 26 and impinges on objective lens 27.

Objective lens 27 directs an illuminating beam 131 onto object 10.

Objective lens 27 collects reflected beam 12 and directs the reflected beam 12 onto first beam splitter 26.

First beam splitter directs the reflected beam 12 to pass through lens 29 and to impinge on first masking module 70.

First masking module 70 may unmask one or more first exit pupil region to allow a passage of collected beam 141 through first masking module 70 and onto first detection module 80.

Figure 5:
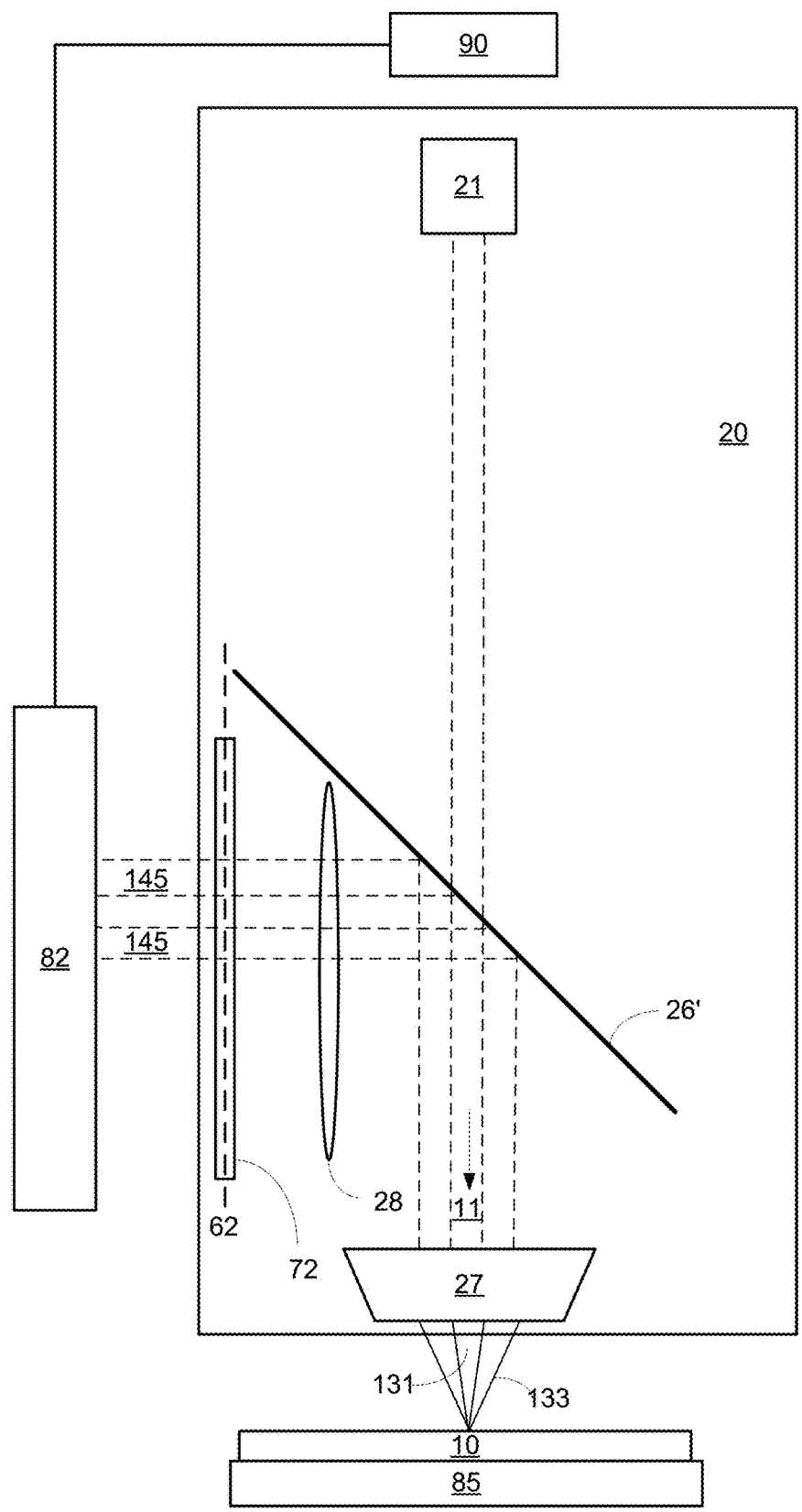
FIG. 5 illustrates a system and an object according to an embodiment of the invention.

FIG. 5 illustrates system 105 and object 10 according to an embodiment of the invention.

System 105 is illustrated as including illumination and collection module 20, second detection module 82, processor 90 and mechanical stage 85.

Illumination and collection module 20 is illustrated as including a radiation source 21, donut mirror 26', objective lens 27, lens 28, and second masking module 72 that is positioned at second exit pupil 62.

Radiation source 21 directs first radiation beam 11 towards donut mirror 26'.

First radiation beam 11 passes through an aperture formed in donut mirror 26' and impinges on objective lens 27.

Objective lens 27 directs an illuminating beam 131 onto object 10.

Objective lens 27 collects reflected beam (not shown) and scattered beam 133 (that surrounds the reflected beam) and directs the reflected beam and the scattered beam 133 onto donut mirror 26'.

Donut mirror 26' directs the scattered beam 133 to pass through lens 28 and to impinge on second masking module 72.

Second masking module 72 may unmask one or more second exit pupil region to allow a passage of collected beam 145 through second masking module 72 and onto second detection module 82.

Figure 6:
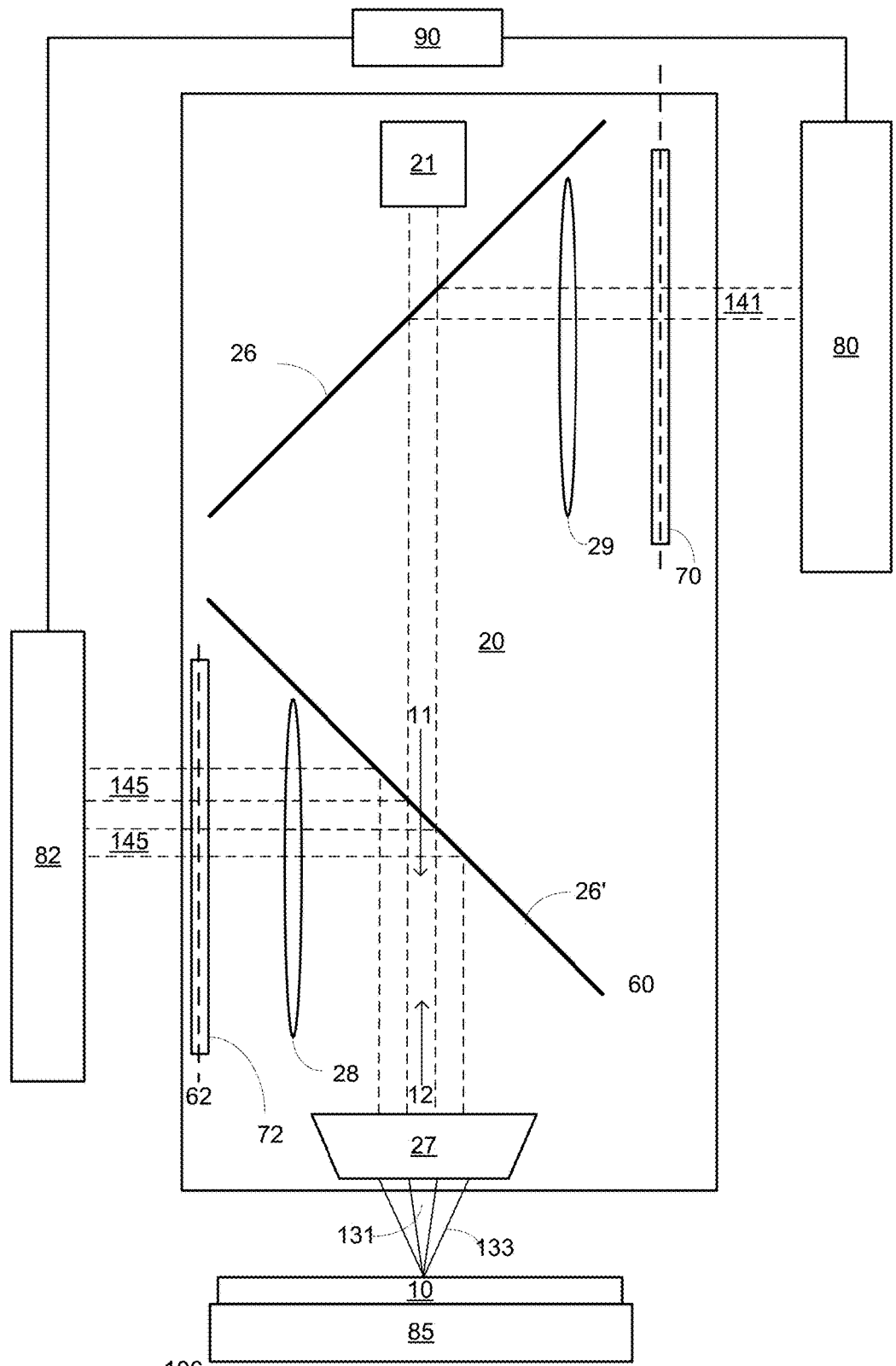
FIG. 6 illustrates a system and an object according to an embodiment of the invention.

FIG. 6 illustrates system 106 and object 10 according to an embodiment of the invention.

System 106 is illustrated as including illumination and collection module 20, first detection module 80, second detection module 82, processor 90 and mechanical stage 85.

Illumination and collection module 20 is illustrated as including a radiation source 21, first beam splitter 26, objective lens 27, lens 29, first masking module 70 that is positioned at first exit pupil 60, donut mirror 26', lens 28, and second masking module 72 that is positioned at second exit pupil 62.

Radiation source 21 directs first radiation beam 11 towards donut mirror 26'.

First radiation beam 11 passes through passes an aperture formed in donut mirror 26' and impinges on objective lens 27.

Objective lens 27 directs an illuminating beam 131 onto object 10.

Objective lens 27 collects reflected beam 12 and directs the reflected beam 12 to pass through the aperture formed in donut mirror 26' and to impinge on first beam splitter 26.

First beam splitter 26 directs the reflected beam 12 to pass through lens 29 and to impinge on first masking module 70.

First masking module 70 may unmask one or more first exit pupil region to allow a passage of collected beam 141 through first masking module 70 and onto first detection module 80.

Objective lens 27 also collects scattered beam 133 and directs the scattered beam 133 towards donut mirror 26'.

Donut mirror 26' directs scattered beam 133 to pass through the lens 28 and to impinge (as second collected beam 145) on second masking module 72.

Second masking module 72 may unmask one or more second exit pupil region to allow a passage of collected beam 145 through second masking module 72 and onto second detection module 82.

Figure 7:
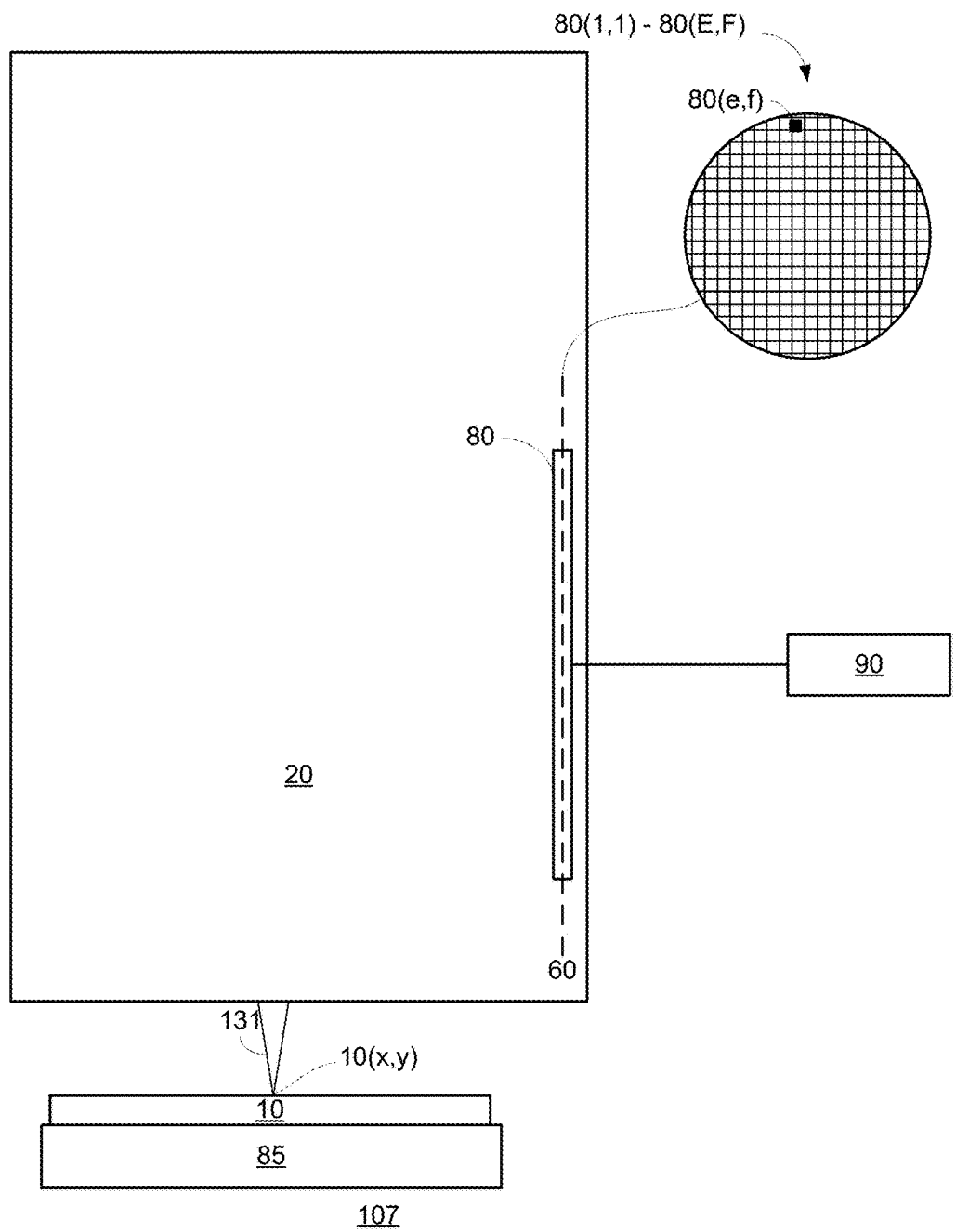
FIG. 7 illustrates a system and an object according to an embodiment of the invention.

FIG. 7 illustrates system 107 and object 10 according to an embodiment of the invention.

System 107 is illustrated as including illumination and collection module 20, first detection module 80, processor 90 and mechanical stage 85.

Illumination and collection module 20 is illustrated as directing an illuminating beam 131 onto object 10.

First detection module 80 is positioned at the first exit pupil and has multiple first detectors 80(1,1)-80(E,F). Each first exit pupil region is "covered" by a dedicated one or more first detector (for example—a single first exit pupil region may be covered by first detector 80(e,f)).

System 107 may perform a single inspection iteration and obtain all the information obtained by system 101 in multiple (R) illumination and collection iterations.

System 107 does not require first masking module 70 of system 101.

Figure 8:
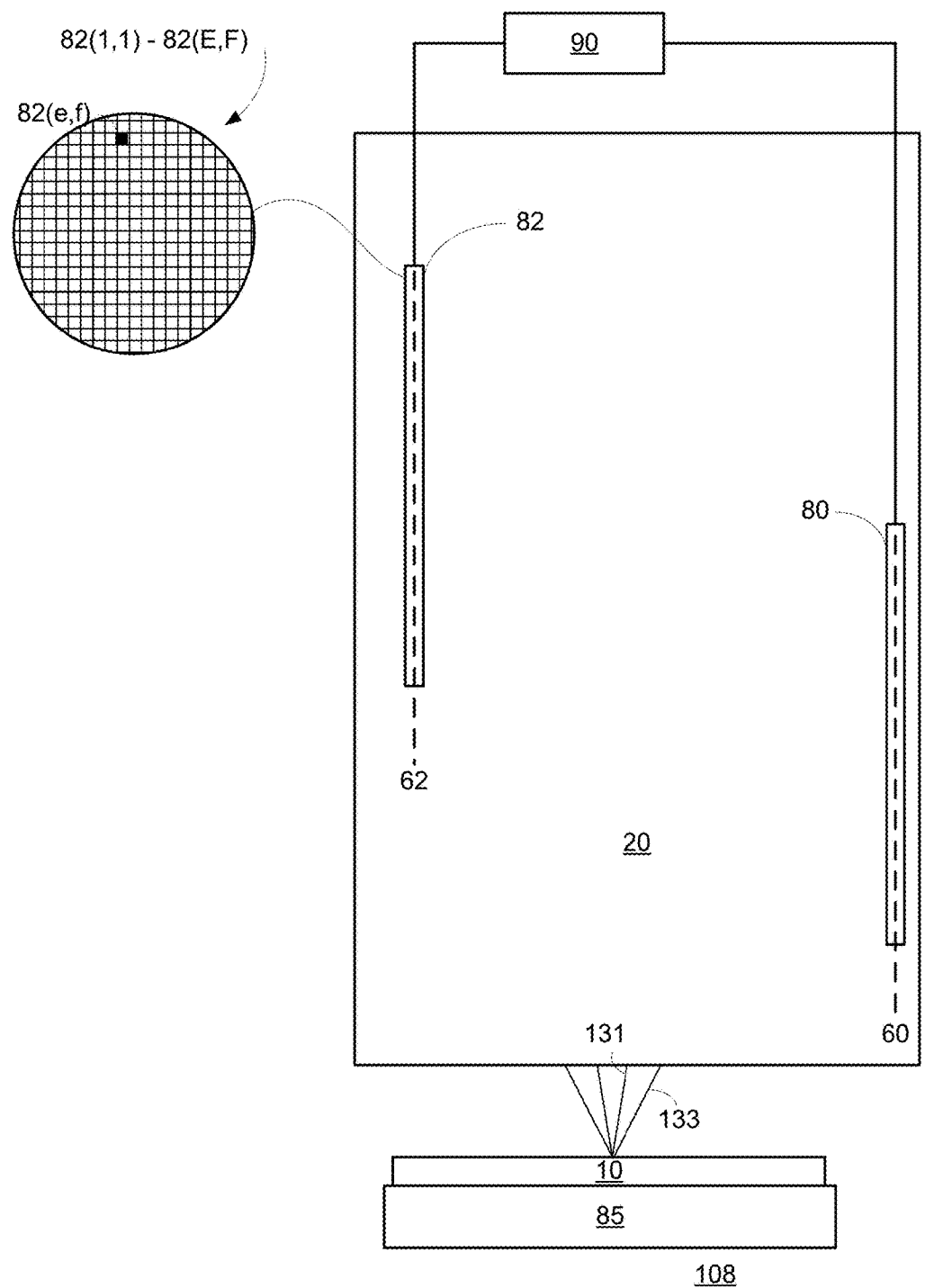
FIG. 8 illustrates a system and an object according to an embodiment of the invention.

FIG. 8 illustrates system 108 and object 10 according to an embodiment of the invention.

System 108 is illustrated as including illumination and collection module 20, first detection module 80, second detection module 82, processor 90 and mechanical stage 85.

Illumination and collection module 20 is illustrated as directing an illuminating beam 131 onto object 10.

First detection module 80 is positioned at the first exit pupil 60 and has multiple first detectors 80(1,1)-80(E,F). Each first exit pupil region is "covered" by a dedicated one or more first detector (for example—a single first exit pupil region may be covered by first detector 80(e,f)).

Second detection module 82 is positioned at the second exit pupil 62 and has multiple second detectors 82(1,1)-82(E,F). Each second exit pupil region is "covered" by a dedicated one or more second detector (for example—a single second exit pupil region may be covered by second detector 82(e,f)).

System 108 may perform a single inspection iteration and obtain all the information obtained by system 103 in multiple (R) illumination and collection iterations.

System 108 does not require first masking module 70 and second masking module 72 of system 106.

Figure 9:
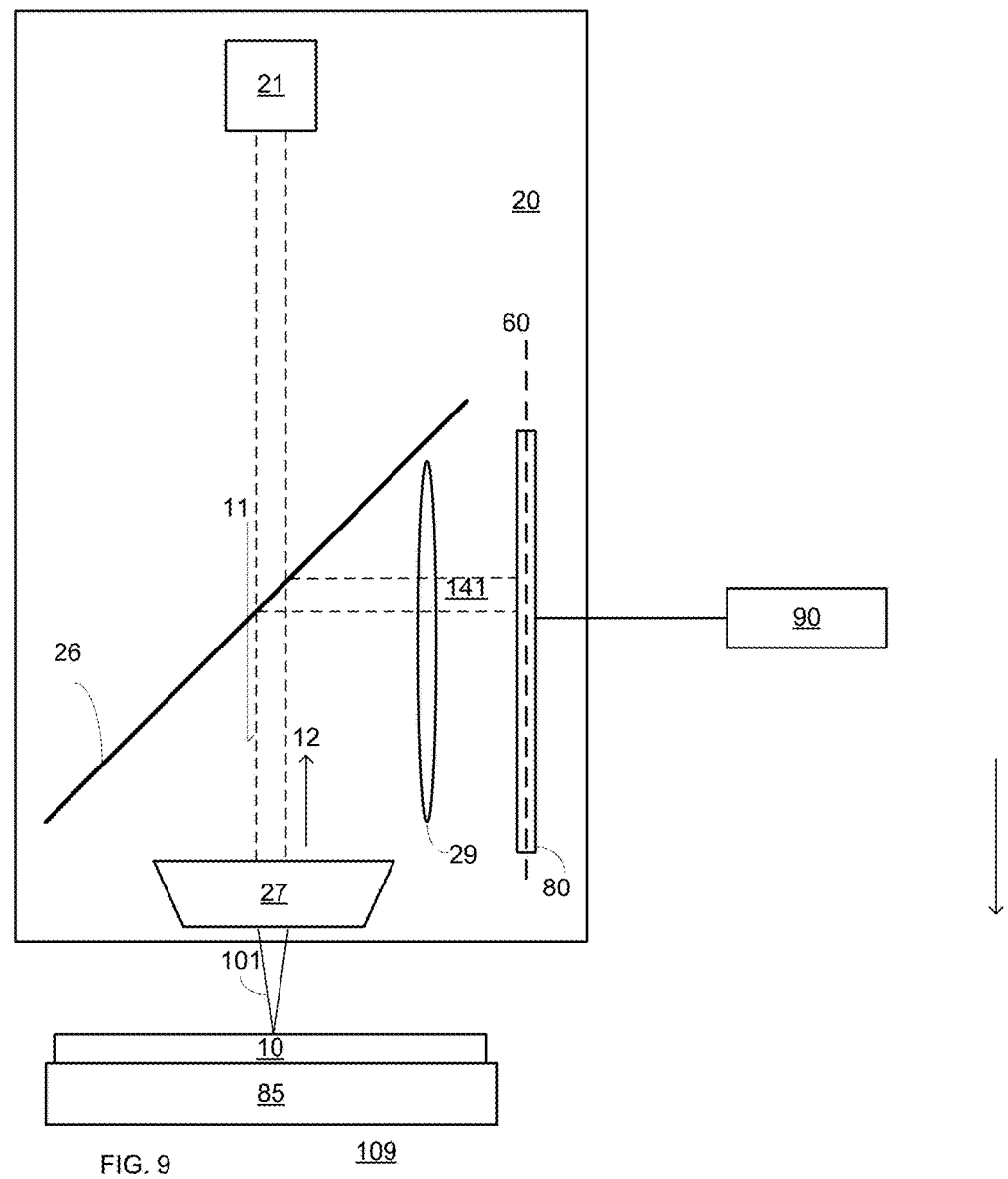
FIG. 9 illustrates a system and an object according to an embodiment of the invention.

FIG. 9 illustrates system 109 and object 10 according to an embodiment of the invention.

System 109 is illustrated as including illumination and collection module 20, first detection module 80, processor 90 and mechanical stage 85.

Illumination and collection module 20 is illustrated as including a radiation source 21, first beam splitter 26, objective lens 27 and lens 29.

First detection module 80 is positioned at first exit pupil 60.

Radiation source 21 directs first radiation beam 11 towards first beam splitter 26.

First radiation beam 11 passes through first beam splitter 26 and impinges on objective lens 27.

Objective lens 27 directs an illuminating beam 131 onto object 10.

Objective lens 27 collects reflected beam 12 and directs the reflected beam 12 onto first beam splitter 26.

First beam splitter directs the reflected beam 12 to pass through lens 29 and to impinge (as first collected beam 141) on first detection module 80.

Figure 10:
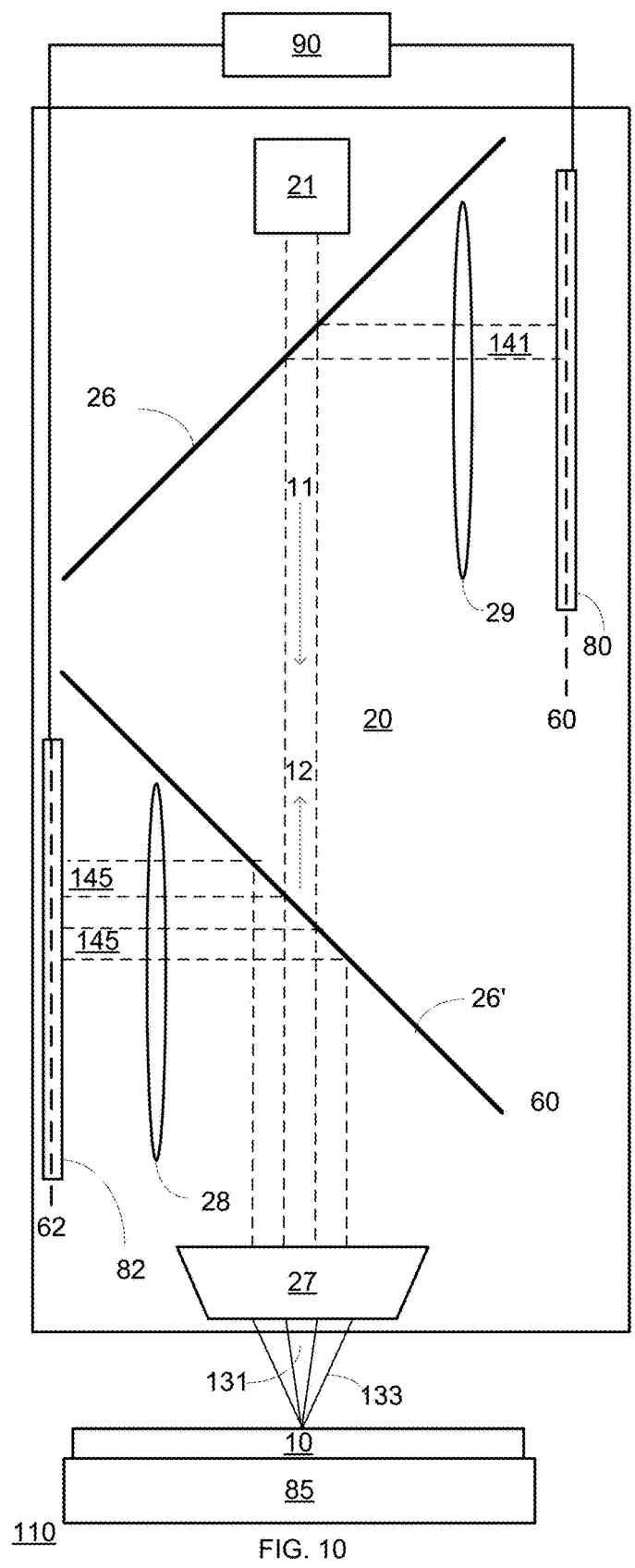
FIG. 10 illustrates a system and an object according to an embodiment of the invention.

FIG. 10 illustrates system 110 and object 10 according to an embodiment of the invention.

System 110 is illustrated as including illumination and collection module 20, first detection module 80, second detection module 82, processor 90 and mechanical stage 85.

Illumination and collection module 20 is illustrated as including a radiation source 21, first beam splitter 26, objective lens 27, lens 29, donut mirror 26' and lens 28. First detection module 80 is positioned at first exit pupil 60. Second detection module 72 is positioned at second exit pupil 62.

Radiation source 21 directs first radiation beam 11 towards donut mirror 26'.

First radiation beam 11 passes through passes an aperture formed in donut mirror 26' and impinges on objective lens 27.

Objective lens 27 directs an illuminating beam 131 onto object 10.

Objective lens 27 collects reflected beam 12 and directs the reflected beam 12 to pass through the aperture formed in donut mirror 26' and to impinge on first beam splitter 26.

First beam splitter 26 directs the reflected beam 12 to pass through lens 29 and to impinge (as first collected beam 141) on first detection module 80.

Objective lens 27 also collects scattered beam 133 and directs the scattered beam 133 towards donut mirror 26'.

Donut mirror 26' directs scattered beam 133 to pass through the lens 28 and to impinge (as third collected beam 145) on second detection module 82.

Figure 11:
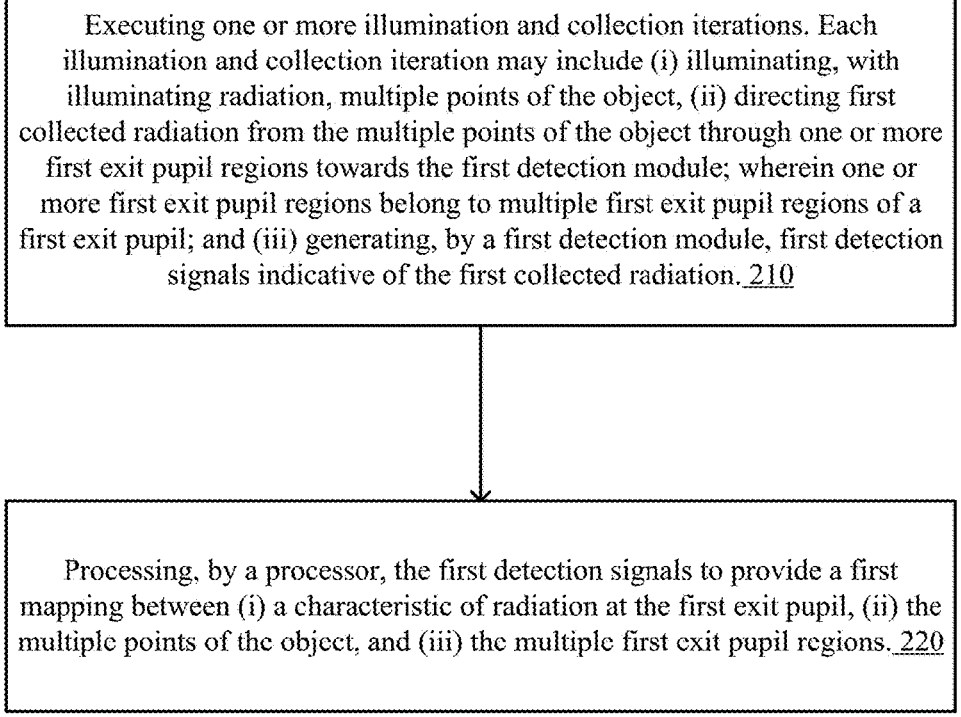
FIG. 11 illustrates a method according to an embodiment of the invention.

FIG. 11 illustrates method 200 according to an embodiment of the invention.

Method 200 may start by step 210 of executing one or more illumination and collection iterations. Each inspection iteration may include (i) illuminating, with illuminating radiation, multiple points of the object, (ii) directing first collected radiation from the multiple points of the object through one or more first exit pupil regions towards the first detection module; wherein one or more first exit pupil regions belong to multiple first exit pupil regions of a first exit pupil; and (iii) generating, by a first detection module, first detection signals indicative of the first collected radiation.

Step 210 may be followed by step 220 of processing, by a processor, the first detection signals to provide a first mapping between (i) a characteristic of radiation at the first exit pupil, (ii) the multiple points of the object, and (iii) the multiple first exit pupil regions.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will be appreciated that conductivity types and polarities of potentials may be reversed.

Each signal described herein may be designed as positive or negative logic. In the case of a negative logic signal, the signal is active low where the logically true state corresponds to a logic level zero. In the case of a positive logic signal, the signal is active high where the logically true state corresponds to a logic level one. Note that any of the signals described herein may be designed as either negative or positive logic signals. Therefore, in alternate embodiments, those signals described as positive logic signals may be implemented as negative logic signals, and those signals described as negative logic signals may be implemented as positive logic signals.

Furthermore, the terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. An inspection system, comprising:
   a first detection module;
   an illumination and collection module; and
   a processor;
   wherein the illumination and collection module and the first detection module are configured to execute a plurality of illumination and collection iterations; wherein each illumination and collection iteration comprises:
   illuminating, by the illumination and collection module and with illuminating radiation, multiple points of an object, each of the multiple points of the object being different from others of the multiple points of the object;
   directing, by the illumination and collection module, collected radiation from the multiple points of the object towards the first detection module; wherein a first portion of the collected radiation is directed through one exit pupil region, the one exit pupil region being one of multiple exit pupil regions that collectively form a first exit pupil of the inspection system; and
   generating, by the first detection module, detection signals that are indicative of the first portion of the collected radiation;
   wherein for each of the plurality of illumination and collection iterations, a different portion of the collected radiation is directed through a different one of the multiple exit pupil regions;
   wherein a number of the plurality of illumination and collection iterations is equal to a number of the multiple exit pupil regions, and
   wherein the processor is configured to process the detection signals from the plurality of illumination and collection iterations to provide a mapping between a characteristic of radiation at each of the multiple exit pupil regions for each of the multiple points of the object.

2. The system according to claim 1 wherein the illumination and collection module comprises a first masking module that is configured to selectively unmask the one exit pupil region during a first illumination and collection iteration, and mask the one exit pupil region during a remainder of the plurality of illumination and collection iterations.

3. The system according to claim 1 wherein the illumination and collection module comprises a first masking module that is configured to selectively mask different ones of the multiple exit pupil regions.

4. The system according to claim 1 wherein the first detection module comprises multiple first detectors that are positioned at the first exit pupil, and wherein each of the multiple detectors corresponds to one of the multiple exit pupil regions.

5. The system according to claim 1 wherein the processor is configured to evaluate, in response to the mapping, an outcome of a first masking operation that masks at least one of the multiple exit pupil regions while unmasking the one exit pupil region.

6. The system according to claim 1 wherein the characteristic of radiation is an intensity of the collected radiation.

7. The system according to claim 1, further comprising a second detection module; wherein each illumination and collection iteration further comprises directing a portion of second collected radiation through one or more predetermined second exit pupil regions towards the second detection module and generating second detection signals indicative of the portion of the second collected radiation; wherein the one or more predetermined second exit pupil regions are ones of multiple second exit pupil regions that collectively form a second exit pupil.

8. The system according to claim 1 wherein the plurality of illumination and collection iterations comprise a plurality of inspection iteration sets; wherein each inspection iteration set comprises: (a) a first inspection iteration during which a single beam of illumination radiation scans the multiple points of the object; (b) a second inspection iteration during which a pair of beams of illumination radiation impinge on the object to provide a pair of spots that (i) are spaced apart from each other by a predefined distance and (ii) scan the multiple points of the object; and (c) a third inspection iteration during which another pair of beams of illumination radiation impinge on the object to provide another pair of spots that (i) are phase shifted from each other by a predefined phase shift and (ii) scan the multiple points of the object.

9. The system according to claim 8 wherein the processor is configured to calculate an S-matrix in response to the detection signals.

10. A method for inspecting an object using an inspection system, the method comprising:
executing a plurality of illumination and collection iterations to provide scan images of the object; wherein each illumination and collection iteration comprises:
illuminating, with illuminating radiation, multiple points of the object, each of the multiple points of the object being different from others of the multiple points of the object,
directing collected radiation from the multiple points of the object towards a first detection module; wherein a first portion of the collected radiation is directed through one exit pupil region, the one exit pupil region being one of multiple exit pupil regions that collectively form a first exit pupil of the inspection system, and
generating, by the first detection module, detection signals indicative of the first portion of the collected radiation,
processing, by a processor, the detection signals from the plurality of illumination and collection iterations to provide a mapping between a characteristic of radiation at each of the multiple exit pupil regions for each of the multiple points of the object, wherein for each of the plurality of illumination and collection iterations, a different portion of the collected radiation is directed through a different one of the multiple exit pupil regions, and wherein a number of the plurality of illumination and collection iterations is equal to a number of the multiple exit pupil regions.

11. The method of claim 10 further comprising selectively unmasking the one exit pupil region during a first illumination and collection iteration, and masking the one exit pupil region during a remainder of the plurality of illumination and collection iterations.

12. A non-transitory computer readable medium that stores instructions that when executed cause the inspection system to perform the method of claim 10.

13. A method for inspecting an object using an inspection system, the method comprising:
executing a plurality of illumination and collection iterations, wherein each illumination and collection iteration comprises:
illuminating, with illuminating radiation, multiple points of the object, each of the multiple points of the object being different from others of the multiple points of the object,
directing collected radiation from the multiple points of the object towards a detection module, wherein a first portion of the collected radiation is directed through an exit pupil region, the exit pupil region being one of the multiple exit pupil regions that collectively form an exit pupil of the inspection system, and
generating, by the detection module, detection signals that are indicative of the first portion of the collected radiation,
processing, by a processor, the detection signals from the plurality of illumination and collection iterations to provide a mapping between a characteristic of radiation at each of the multiple exit pupil regions for each of the multiple points of the object, wherein for each of the plurality of illumination and collection iterations, a different portion of the collected radiation is directed through a different one of the multiple exit pupil regions, and wherein a number of the plurality of illumination and collection iterations is equal to a number of the multiple exit pupil regions.

14. The method of claim 13 further comprising selectively unmasking the exit pupil region during a first illumination and collection iteration, and masking the exit pupil region during a remainder of the plurality of illumination and collection iterations.

15. A non-transitory computer readable medium that stores instructions that when executed cause the inspection system to perform the method of claim 13.

* * * * *